United States Patent [19]

Patton et al.

[11] Patent Number: 5,149,875
[45] Date of Patent: * Sep. 22, 1992

[54] HALOGENATION OF AROMATIC AMINE COMPOUNDS

[75] Inventors: Jerry R. Patton; Narayanasamy Gurusamy, both of Ballwin, Mo.

[73] Assignee: Mallinckrodt Specialty Chemicals Company, St. Louis, Mo.

[*] Notice: The portion of the term of this patent subsequent to Oct. 1, 2008 has been disclaimed.

[21] Appl. No.: 641,396

[22] Filed: Jan. 15, 1991

Related U.S. Application Data

[63] Continuation-in-part of Ser. No. 472,930, Jan. 31, 1990, Pat. No. 5,053,542.

[51] Int. Cl.$^5$ .................................. C07C 209/74
[52] U.S. Cl. .................................................... 564/412
[58] Field of Search ........................................ 564/412

[56] References Cited

U.S. PATENT DOCUMENTS

| | | | |
|---|---|---|---|
| 3,987,057 | 10/1976 | Goddard | 71/96 X |
| 4,138,242 | 2/1979 | Goddard | 71/92 |
| 4,443,631 | 4/1984 | Padilla | 564/412 |
| 5,053,542 | 10/1991 | Patton et al. | 564/412 |

*Primary Examiner*—Richard L. Raymond
*Attorney, Agent, or Firm*—Rothwell, Figg, Ernst & Kurz

[57] ABSTRACT

Aromatic amine compounds are halogenated in the presence of a quaternary ammonium halide.

26 Claims, No Drawings

HALOGENATION OF AROMATIC AMINE COMPOUNDS

CROSS-REFERENCE TO RELATED APPLICATION

This application is a continuation-in-part of U.S. Ser. No. 472,930, filed Jan. 31, 1990, now U.S. Pat. No. 5,053,542.

BACKGROUND OF THE INVENTION

1. Field of the Invention

The present invention relates to halogenation of aromatic amine compounds.

2. Description of the Background Art

Halogenated aromatic amine compounds are useful as chemical intermediates. For example, 2,4-dihaloanilines, such as 4-bromo-2-fluoroaniline, are useful, inter alia, in the preparation of pharmaceutical and agricultural chemicals. The preparation of certain of these useful chemical intermediates has previously often been cumbersome and expensive. Prior art processes for the production of 4-bromo-2-fluoroaniline, for example, may require the use of expensive and/or difficult to obtain brominating agents.

One process for the preparation of 4-bromo-2-fluoroaniline (and its use in the preparation of arylpropionic acids) is taught in U.S. Pat. No. 4,443,631 to Padilla, issued April 17, 1984. 1,3-dibromo-5,5-dimethylhydantoin in dimethylformamide (DMF) is prepared under nitrogen and is added to a solution of 2-fluoroaniline in DMF maintained at $-34°$ to $-23°$ C. with a dry ice-acetone bath. Other brominating agents reportedly useful are N-bromamides or -imides such as N-bromoacetamide or N-bromosuccinimide.

U.S. Pat. No. 3,987,057 (Goddard, Oct. 19, 1976) references the production of 4-bromo-2-fluoroaniline from 2-fluoroaniline and N-bromo-succinimide.

U.S. Pat. No. 4,138,242 (Goddard, Feb. 6, 1979) relates to herbicidal compounds and their preparation from 4-chloro-2-fluoroaniline. The 4-chloro-2-fluoroaniline is prepared through the chlorination of 2-fluoroacetanilide to yield 4-chloro2-fluoroacetanilide and the subsequent formation of the desired aniline.

There remains a need in the art for a new, simple, safe and relatively inexpensive process for the halogenation of aromatic amine compounds.

SUMMARY OF THE INVENTION

In accordance with the present invention, a process for halogenating an aromatic amine compound comprises forming a mixture including an aromatic amine compound in a quaternary ammonium halide, and halogenating the aromatic amine compound in the presence of the quaternary ammonium halide in the mixture.

DETAILED DESCRIPTION OF THE PREFERRED EMBODIMENTS

The process of the present invention can be used to halogenate various aromatic amine compounds.

The term "aromatic amine compound" generally refers to compounds in which nitrogen is attached directly to an aromatic ring, such as aniline and its derivatives. Suitable derivatives of aniline to which the invention is applicable include 2-fluoroaniline, 3-fluoroaniline, 4-fluoroaniline, 2,4-difluoroaniline, p-toluidine and the like.

In the process of the present invention, a mixture is formed which includes an aromatic amine compound and a quaternary ammonium halide. The aromatic amine compound is halogenated in the mixture in the presence of the quaternary ammonium halide. The aromatic amine can be halogenated in the mixture utilizing a halogenating agent, such as molecular halogen. Examples of molecular halogen include molecular bromine and molecular chlorine. In particularly preferred embodiments, molecular halogen is mixed with a corresponding quaternary ammonium halide (for example, molecular bromine and quaternary ammonium bromide), so as to form a quaternary ammonium trihalide, prior to addition of the aromatic amine compound. When the aromatic amine compound is added to the quaternary ammonium trihalide, the aromatic amine compound is halogenated by the quaternary ammonium trihalide. As used herein, the term quaternary ammonium halide can also encompass quaternary ammonium trihalides. Selectivity is improved when using a quaternary ammonium trihalide as the halogenating agent. For example, formation of a quaternary ammonium tribromide prior to addition of the aromatic amine compound provides for better bromination selectivity than merely mixing the aromatic amine, quaternary ammonium bromide and molecular bromine.

In preferred embodiments, the reaction mixture includes an inert solvent. Prior to addition of the aromatic amine compound, the molecular halogen and the quaternary ammonium halide are mixed in the inert solvent in a molecular (molar) ratio that ranges from about 1:1 to about 1.05:1. Preferably, the ratio is about 1:1.

An aromatic amine compound can be halogenated in accordance with the present invention so as to form a halogenated aromatic amine hydrohalide salt. If desired, the halogenated aromatic amine hydrohalide salt can be neutralized to form a halogenated aromatic amine product.

A preferred embodiment of the present invention involves further halogenation of a haloaniline such as 2-fluoroaniline, 3-fluoroaniline, 4-fluoroaniline, 2,4-difluoroaniline or the like. This process can be utilized to form a further halogenated haloaniline hydrohalide salt, which can be neutralized to produce a further halogenated haloaniline compound.

The process of the present invention can be used to produce various 2,4-dihaloanilines.

In accordance with one aspect of the invention, a 2,4-dihaloaniline is prepared by halogenating a 2-haloaniline in the presence of a quaternary ammonium trihalide catalyst and then neutralizing the resulting 2,4-dihaloaniline hydrohalide salt.

Preferably, the 2,4-dihaloaniline is prepared via a continuous process wherein a 2-haloaniline is added to a quaternary ammonium trihalide catalyst formed by mixing molecular halogen with a corresponding quaternary ammonium halide in an inert solvent. The dihaloaniline precipitates as its hydrohalide salt which is readily recovered and then neutralized to yield the free compound. In the event the hydrohalide salt is to be used in a subsequent reaction, neutralization is omitted. The process consumes essentially all of the molecular halogen, and the remaining quaternary ammonium halide in the solvent can be recycled for further use. Operation of the present process in the batch mode also is possible.

In a preferred embodiment, the 2,4-dihaloaniline produced is 2-bromo-4-fluoroaniline.

The inert solvent selected for the reaction mixture can be chosen from a variety of known inert solvents. Aprotic solvents generally are useful so long as the reactants are soluble therein and the halogenated salt product is not. Hexane, heptane, carbon tetrachloride and chloroform are suitable solvents for use in the process. In preferred embodiments, the solvent for the process of this invention is dry methylene chloride. In particularly preferred embodiments, the solvent is employed in relative excess of the reactants in order to facilitate separation of the desired end product and handling of the reaction by-products.

The solvent containing the molecular halogen and quaternary ammonium halide is stirred at room temperature to form the quaternary ammonium trihalide. The 2-haloaniline to be halogenated is added to the mixture at ambient temperature while stirring, usually resulting in an immediate slight exotherm. The ratio of 2-haloaniline to molecular halogen desirably ranges from about 0.8:1 to 1:1, with the 1:1 ratio being preferred. The reaction goes to completion virtually immediately.

The temperature of the mixture containing the desired reaction product is lowered (for example, a cooling jacket or cooling loop, whereupon the hydrohalide salt of the 2,4-dihaloaniline (e.g., hydrobromide salt of 4-bromo-2-fluoroaniline) precipitates. The precipitated hydrohalide salt is easily removed from the solution via centrifugation and/or filtration. The hydrohalide salt can be slurried or suspended in a suitable liquid such as water or an aqueous solution such as methylene chloride solution, neutralized at basic pH (preferably between pH 7 and 8), and the layers separated. The layer from which the product has separated can be evaporated (for example, by rotovapor) to leave the oily product. Yields of approximately 95 percent have been achieved in a continuous-mode version of the process, and can be even higher in batch mode.

The solvent-catalyst solution remaining after removal of the precipitated hydrohalide salt can be recycled for further use by the subsequent addition of halogen and 2-haloaniline. This recycling further increases yields.

The usefulness and advantages of the present invention are reflected in its high yield and high specificity to the desired 2,4-dihaloaniline.

The following examples are provided for illustrative purposes and are not to be construed as limiting.

EXAMPLE 1

33.5 g (0.104 mol) of tetrabutylammonium bromide were slowly added over 5 minutes to 100 ml of dry methylene chloride at ambient temperature in a glass vessel with stirring. 16.5 g (0.103 mol) of molecular bromine in 10 ml dry methylene chloride were added with stirring. The temperature rose from 20° C. to 38° C. After 10 minutes 11.33 g (0.103 mol) of 2-fluoroaniline were added in one portion. The temperature quickly rose from 20° C. to 40° C. The vessel was placed in an ice bath, and the temperature quickly returned to ambient. A precipitate formed on cooling. The precipitate was filtered, washed with fresh, dry methylene chloride and weighed. 8.6 g were recovered.

The reaction medium was reused in a second reaction. 16.5 g (0.103 mol) of molecular bromine were added along with 4.9 g tetrabutylammonium bromide to replace catalyst lost in transfers. The procedure was repeated with 11.3 g (0.103 mol) of 2-fluoroaniline. The total recovery from both reactions was 27.1 g 4-bromo-2-fluoroaniline hydrobromide, a 97 percent yield.

EXAMPLE 2

The procedure of Example 1 was repeated using catalyst in molar excess over molecular bromine, which was in molar excess over the 2-fluoroaniline. The quantities used were 45.1 g (0.14 mol) tetrabutylammonium bromide
19.2 g (0.12 mol) molecular bromine
10.9 g (0.10 mol) 2-fluoroaniline
130 ml dry methylene chloride were used. A trace of dibrominated fluoroaniline was detected in the recovered product by LC analysis.

EXAMPLE 3

Preparation of 4-bromo-2-fluoroaniline by Iterative Process

Cycle 1. Methylene chloride, 125 ml, and 32.2 g (0.1 mol) tetrabutylammonium bromide were mixed in a 200-ml, 3-necked roundbottom flask, equipped with a mechanical stirrer, a thermometer, an additional funnel and a water condenser leading to a mineral oil bubbler. Bromine, 16.0 g (0.1 mol), was added to the mixture over 15 minutes at room temperature. The temperature of the mixture rose from 24° C. to 30° C. The contents of the flask were stirred for 30 minutes. 2-fluoroaniline, 11.1 g (0.1 mol), at room temperature, was added to the mixture in one portion. The temperature of the mixture rose to 40° C. The orange solution immediately turned yellowish. After stirring for 15 minutes, the solution turned milky and the temperature was 32° C. After 30 more minutes, solids were observed. The solution was filtered and the solids washed with ice-cold methylene chloride until white. On air-drying 9 g of product (Solid I) was obtained. The melting point was >200° C. LC analysis showed only desired product with a trace of impurity. LC analysis of the mother liquor (I) showed that it contained some desired product and some dibrominated compound.

Cycle 2. The mother liquor I was placed in the same apparatus described for Cycle I. Bromine, 16.0 g (0.1 mol), was added to it at room temperature. The reddish suspension was stirred for 10 minutes, and 11.1 g (0.1 mol) 2-fluoroaniline were added in one portion at room temperature. After 15 minutes, the solution was a milky suspension. After stirring for an additional hour, the solids were filtered off, washed with ice-cold methylene chloride and air-dried to yield 20 g (Solid II). The mother liquor (II) was brownish in color and LC analysis showed it contained desired product, some unreacted 2-fluoroaniline and some dibrominated impurity.

Cycle 3. The mother liquor II was again mixed with bromine, 16.0 g (0 1 mol), and 2-fluoroaniline, 11.1 g (0.1 mol), was added as above. After stirring for 30 minutes, the white solid was filtered off and washed. 12 g (Solid III) were obtained. The mother liquor (III) was analyzed and again contained product, 2-fluoroaniline and impurity.

Cycle 4. The mother liquor III was used to repeat the previous step. The reaction mixture was stirred for 2 hours after the 2-fluoroaniline was added and then allowed to stand at room temperature overnight. Solid IV, 28 g, was isolated as above.

Cycle 5. The mother liquor IV was used to repeat the previous steps. The reaction mixture was stirred for 3 hours after the 2-fluoroaniline was added. The white solids were isolated, yielding 28 g. The brownish mother liquor was analyzed by LC and found to contain some desired product with minor amounts of 2-fluoroaniline and dibrominated impurity.

Salt Neutralization. All solids from Cycle I to Cycle 5 were combined for a total of 97 g, 71% of theory. The salt was dissolved in 200 ml methylene chloride and the solution was stirred while adding dilute sodium hydroxide until it was neutral to litmus. The methylene chloride layer was separated, washed three times with 200 ml portions of water and evaporated in a rotovapor to yield 65 g of a light yellow oil. Fractional distillation produced the following:

| | |
|---|---|
| Precut | 6 g, analyzed as product and 2-fluoroaniline (added to mother liquor for subsequent workup); |
| Main Cut | 51 g, analyzed by capillary LC to be 99% pure 4-bromo-2-fluoroaniline and 0.776% dibrominated impurity; |
| Pot Residue | analyzed as product and a considerable amount of the dibrominated impurity (also added to mother liquor for workup). |

NMR analyses of the Main Cut confirmed the structure to be the desired product.

Mother Liquor Workup. The mother liquor V was combined with the Precut and the Pot Residue from the salt neutralization step. The combined mixture was neutralized with dilute sodium hydroxide solution to neutral by litmus, washed twice with 200 ml portions of water, dried using a molecular sieve and evaporated in a rotovapor to yield 55 g of a brownish viscous oil. Fractional distillation under pump vacuum yielded a 30 g Main Cut that was 90% desired product by LC analysis.

The total isolated yield was 81 g, 85% of theory.

EXAMPLE 4

2-bromo-4-fluoroaniline was formed utilizing the following starting ingredients:

| Reactants | Weight | Moles |
|---|---|---|
| 4-fluoroaniline | 11.1 g | 0.1 |
| $CH_2Cl_2$ | | 125 ml |
| $Bu_4N^+Br^-$ | 32.2 g | 0.1 |
| Bromine | 16.0 g | 0.1 |

Tetrabutylammonium tribromide was formed in solution by adding bromine to a stirred solution of tetrabutylammonium bromide ($Bu_4N^+Br^-$) in methylene chloride ($CH_2Cl_2$). The 4-fluoroaniline was added all at once and an exotherm to 42° C. was noted. After stirring for 2 hours at ambient temperature, the solution was filtered to give a white solid which was air dried. This solid was dissolved in water, neutralized with 20% NaOH (aqueous) to give 14.9 g of yellow oil. Analysis showed 93% pure 2-bromo-4-fluoroaniline with the remainder being starting 4-fluoroaniline. An additional 2.5 g was isolated from the mother liquor which can be recycled. A total yield of 85% was realized with recovered starting material being recovered for recycle.

EXAMPLE 5

The same procedure as Example 4 was run with the exception that 3-fluoroaniline was substituted for 4-fluoroaniline, using 0.1 mole of each reactant. The major product was the expected 4-bromo-3-fluoroaniline, but another isomer also was formed, 2-bromo-5-fluoroaniline. A repeat of this experiment showed that a 95:4 ratio of the isomers could be achieved with approximately 64% conversion.

EXAMPLE 6

The bromination of 2,4-difluoroaniline using tetrabutylammonium tribromide was carried out using the procedures generally set out in Example 4, but substituting 2,4-difluoroaniline for 4-fluoroaniline, with 0.1 mole of corresponding starting materials. The reaction was not optimized and a yield of approximately 60% 6-bromo-2,4-fluoroaniline was obtained.

EXAMPLE 7

To show that selectivity is still obtained using a highly activated aniline, bromination of p-toluidine using tetrabutylammonium tribromide was carried out as generally described in Example 4, but substituting p-toluidine for 4-fluoroaniline, on a 0.75 mole reaction. The desired product 2-bromo-4-methylaniline was obtained in 66% yield on the 0.75 mole reaction.

Although the invention has been described in connection with certain preferred embodiments and specific Examples, it is not so limited. Modifications within the scope of the claims will be readily apparent to those skilled in the art.

We claim:

1. A process for halogenating an aromatic amine compound, comprising forming a mixture including an aromatic amine compound and quaternary ammonium halide, and halogenating the aromatic amine compound in the presence of the quaternary ammonium halide in said mixture.

2. The process of claim 1, wherein the aromatic amine compound is halogenated in said mixture so as to form a halogenated aromatic amine hydrohalide salt.

3. The process of claim 2, further including the step of neutralizing said salt so as to produce a halogenated haloaniline compound.

4. The process of claim 1, wherein said aromatic amine compound is selected from the group consisting of 2-fluoroaniline, 3-fluoroaniline, 4-fluoroaniline, 2,4-difluoroaniline and p-toluidine.

5. The process of claim 1, wherein said mixture includes molecular halogen for halogenating the aromatic amine compound.

6. The process of claim 5, wherein the quaternary ammonium halide corresponds to said molecular halogen.

7. The process of claim 6, wherein said halogen is bromine.

8. The process of claim 1, wherein said mixture includes an inert solvent.

9. The process of claim 8, wherein said inert solvent is methylene chloride.

10. The process of claim 2, wherein the halogenated aromatic amine hydrohalide salt is neutralized by adding said salt to an aqueous solution having a basic pH.

11. The process of claim 10, wherein said pH is between about 7 and about 8.

12. The process of claim 1, wherein the quaternary ammonium halide is a quaternary ammonium trihalide.

13. The process of claim 12, wherein the quaternary ammonium trihalide is quaternary ammonium tribromide.

14. A process for further halogenating a haloaniline compound, comprising forming a mixture including a haloaniline compound and a quaternary ammonium halide, and halogenating the haloaniline compound in the presence of the quaternary ammonium halide in said mixture.

15. The process of claim 14, wherein the haloaniline compound is halogenated in said mixture so as to form a further halogenated haloaniline hydrohalide salt.

16. The process of claim 15, further including the step of neutralizing said salt so as to produce a further halogenated haloaniline compound.

17. The process of claim 14, wherein said haloaniline compound is selected from the group consisting of 2-fluoroaniline, 3-fluoroaniline, 4-fluoroaniline and 2,4-difluoroaniline.

18. The process of claim 14, wherein said mixture includes molecular halogen for halogenating the haloaniline compound.

19. The process of claim 18, wherein the quaternary ammonium halide corresponds to said molecular halogen.

20. The process of claim 19, wherein said halogen is bromine.

21. The process of claim 14, wherein said mixture includes an inert solvent.

22. The process of claim 21, wherein said inert solvent is methylene chloride.

23. The process of claim 15, wherein the further halogenated haloaniline hydrohalide salt is neutralized by adding said salt to an aqueous solution having a basic pH.

24. The process of claim 23, wherein said pH is between about 7 and about 8.

25. The process of claim 14, wherein the quaternary ammonium halide is a quaternary ammonium trihalide.

26. The process of claim 25, wherein the quaternary ammonium trihalide is quaternary ammonium tribromide.

* * * * *

UNITED STATES PATENT AND TRADEMARK OFFICE
CERTIFICATE OF CORRECTION

PATENT NO. : 5,149,875

DATED : September 22, 1992

INVENTOR(S) : Patton et al.

It is certified that error appears in the above-identified patent and that said Letters Patent is hereby corrected as shown below:

Column 1, line 44, delete "4-chloro2-fluoroacetanilide" and insert --4-chloro-2-fluoroacetanilide--.

Column 3, line 23, after "example," insert --to about 20°C) by conventional means, for example,--.

Signed and Sealed this

Nineteenth Day of October, 1993

Attest:

BRUCE LEHMAN

*Attesting Officer*   *Commissioner of Patents and Trademarks*

REEXAMINATION CERTIFICATE (2506th)

United States Patent [19]
Patton et al.

[11] B1 5,149,875
[45] Certificate Issued * Mar. 14, 1995

[54] HALLOGENATION OF AROMATIC AMINE COMPOUNDS

[75] Inventors: Jerry R. Patton; Narayanasany, Gurusamy, both of Ballwin, Mo.

[73] Assignee: Mallinckrodt Specialty Chemicals Company, St. Louis, Mo.

Reexamination Request:
No. 90/003,362, Mar. 18, 1994

Reexamination Certificate for:
Patent No.: 5,149,875
Issued: Sep. 22, 1992
Appl. No.: 641,396
Filed: Jan. 15, 1991

[*] Notice: The portion of the term of this patent subsequent to Oct. 1, 2008 has been disclaimed.

Certificate of Correction issued Oct. 19, 1993.

Related U.S. Application Data

[63] Continuation-in-part of Ser. No. 472,930, Jan. 31, 1990, Pat. No. 5,053,542.

[51] Int. Cl.[6] .......................................... C07C 209/74
[52] U.S. Cl. ..................................................... 564/412
[58] Field of Search ........................................ 564/412

[56] References Cited

U.S. PATENT DOCUMENTS

| | | | |
|---|---|---|---|
| 3,987,057 | 10/1976 | Goddard | 71/96 X |
| 4,138,242 | 2/1979 | Goodard | 71/92 |
| 4,443,631 | 4/1984 | Padilla | 564/412 |

OTHER PUBLICATIONS

The Chemistry of the Amino Group, Edited by Saul Patai, The Hebrew University, Jerusalem, Israel, 1968, Interscience Publishers.
Bromation régiosélective en série aromatique. I: Monobromation en position *para* de phénois et d'amines aromatiques par le tribromure de tétrabutylammonium, , J. Berthelot et al, Can. J. Chem. 67, 2061 (1989).
Regioselective Bromination in the Aromatic Series. I: Monobromination in Para Position of Phenols and Aromatic Acids by Tetrabutylamonnium Tribromide, J. Berthelot et al, Can. J. Chem. 67, 2061 (1989).
Regioselective Monobromination of Aromatic Amines with Tetrabutylammonium Tribromide, J. Berthelot et al., Synth. Commun., 16, 1641 (1986).
Halogenation Using Quaternary Ammonium Polyhalides. VI. Bromination of Aromatic Amines by Use of Benzyltrimethylammonium Tribromide, Shoji Kajigaeshi et al, Feb. 1988, The Chemical Society of Japan.
Selective Bromination of Aromatic Amines by Use of Tetrbutylammonium Tribromide and Benzyltrimethylammonium Tribromide, Takaaki et al., Res. Rep. of Ube Tech. Coll., No. 35 Mar., 1989.
Selected Experiments in Organic Chemistry, Second Edition, George K. Helmkamp and Harry W. Johnson, Jr., University of California, Riverside, 1968.
Advanced Organic Chemistry, Reactions, Mechanisms, and Structure, Second Edition, Jerry March, Adelphi University, 1977.

*Primary Examiner*—Richard L. Raymond

[57] ABSTRACT

Aromatic amine compounds are halogenated in the presence of a quaternary ammonium halide.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 4 and 17 are cancelled.

Claims 1, and 14 are determined to be patentable as amended.

Claims 2, 3, 5–13, 15, 16 and 18–26, dependent on an amended claim, are determined to be patentable.

1. A process for halogenating an aromatic amine compound, comprising forming a mixture including an aromatic amine compound and quaternary ammonium halide, and halogenating the aromatic amine compound in the presence of the quaternary ammonium halide in said mixture, *said aromatic amine compound being selected from the group consisting of 2-fluoroaniline, 3-fluoroaniline, 4-fluoroaniline, and 2,4-difluoroaniline.*

14. A process for further halogenating a haloaniline compound, comprising forming a mixture including a haloaniline compound and a quaternary ammonium halide, and halogenating the haloaniline compound in the presence of the quaternary ammonium halide in said mixture, *said aromatic amine compound being selected from the group consisting of 2-fluoroaniline, 3-fluoroaniline, 4-fluoroaniline, and 2,4-difluoroaniline.*

* * * * *